United States Patent
Schütze et al.

(10) Patent No.: US 10,648,969 B2
(45) Date of Patent: May 12, 2020

(54) METHOD AND DEVICE FOR QUALITY CONTROLLING A BLOOD-BASED PRODUCT

(71) Applicant: CellTool GmbH, Bernried (DE)

(72) Inventors: Raimund Schütze, Tutzing (DE); Karin Schütze, Tutzing (DE)

(73) Assignee: CellTool GmbH, Bernried (DE)

( * ) Notice: Subject to any disclaimer, the term of this patent is extended or adjusted under 35 U.S.C. 154(b) by 0 days.

(21) Appl. No.: 15/124,171

(22) PCT Filed: Mar. 6, 2015

(86) PCT No.: PCT/EP2015/054724
§ 371 (c)(1),
(2) Date: Sep. 7, 2016

(87) PCT Pub. No.: WO2015/132384
PCT Pub. Date: Sep. 11, 2015

(65) Prior Publication Data
US 2017/0219568 A1 Aug. 3, 2017

(30) Foreign Application Priority Data
Mar. 7, 2014 (DE) ........................ 10 2014 003 386

(51) Int. Cl.
*G01N 33/50* (2006.01)
*G01N 21/65* (2006.01)
*G01N 33/80* (2006.01)
*G01N 33/15* (2006.01)
*G01N 33/49* (2006.01)

(52) U.S. Cl.
CPC ......... *G01N 33/5091* (2013.01); *G01N 21/65* (2013.01); *G01N 33/15* (2013.01); *G01N 33/49* (2013.01); *G01N 33/5094* (2013.01); *G01N 33/80* (2013.01); *G01N 2201/12* (2013.01); *G01N 2333/195* (2013.01)

(58) Field of Classification Search
None
See application file for complete search history.

(56) References Cited

U.S. PATENT DOCUMENTS

2006/0211130 A1* 9/2006 Macioszek ........... C12Q 1/6813
436/174
2010/0136609 A1 6/2010 Bradford et al.

FOREIGN PATENT DOCUMENTS

| CN | 1242937 | 2/2006 | |
|---|---|---|---|
| WO | WO-2006130921 A1 * | 12/2006 | ............. G01N 1/658 |
| WO | 2008027942 | 3/2008 | |
| WO | 2010048678 | 5/2010 | |
| WO | 2014007759 | 1/2014 | |

OTHER PUBLICATIONS

Saade et al. Spectroscopy (2008) 22: 387-395 (Year: 2008).*
Hobro et al. Analyst (Mar. 7, 2013) 138: 3927-3933 (Year: 2013).*
Dasgupta et al. J. Biomed. Optics (2011) 16(7): 07709, pp. 1-9 (Year: 2011).*
Nam et al. Tropical Med. International Health (2010) 15(12): 1436-1441 (Year: 2010).*
Karin Schütze et al., "Laser World of Photonics—DGLM Application Panel Unmet Needs in Photonics and Medicine: Novel cell analysis based on Raman spectroscopy." Photon Lasers Med, Jan. 1, 2013, vol. 2, pp. 361-369.
S. Koch et al., "Novel cell identification: markerfree and suitable for living cells." Proceedings of SPIE, Jun. 18, 2013 SPIE—ISSN 0277-786X, Jun. 18, 2013, vol. 8798, p. 87980J.
Jürgen Luhm et al., "Potential use of Raman Spectroscopy in the Quality Control of blood products." http://celltool.de/files/201311 luhm-drk_raman_red.pdf, published on the web Nov. 1, 2013.

* cited by examiner

*Primary Examiner* — Blaine Lankford
(74) *Attorney, Agent, or Firm* — Sand, Sebolt & Wernow Co., LPA

(57) ABSTRACT

A method and device for quality controlling a blood-based product. In order to control the quality of a blood-based product which comprises an erythrocyte concentrate, a thrombocyte concentrate, a granulocyte concentrate, a leukocyte concentrate, whole blood and/or blood plasma, a Raman spectrum is recorded. By means of evaluating the Raman spectrum, it is determined whether the blood-based product can be used for a transfusion.

11 Claims, 6 Drawing Sheets

METHOD AND DEVICE FOR QUALITY CONTROLLING A BLOOD-BASED PRODUCT

FIELD OF THE INVENTION

The invention relates to methods and devices for quality controlling a blood-based product. The invention in particular relates to such methods and devices by means of which it can be determined whether an erythrocyte concentrate, a thrombocyte concentrate, a granulocyte concentrate, a leukocyte concentrate, a reserve with whole blood and/or a reserve with blood plasma may still be used for transfusion.

BACKGROUND OF THE INVENTION

Blood-based products such as for example erythrocyte concentrates, thrombocyte concentrates, granulocyte concentrates, leukocyte concentrates, whole blood reserves or blood plasma reserves, are today used to a large extent in hospitals in the form of blood reserves. The obtainment of concentrates from human blood donors for transfusion is a complex process. Under ideal storage conditions at a temperature of between 2° C. and 6° C., the storage life of the reserves with erythrocyte concentrate is for example 42 days. Typically up to now, thrombocyte reserves have had to be discarded after a shorter time period.

The quality controlling of blood-based products is often carried out by corresponding confirmations from specialist personnel that a cold chain has been maintained. Since an interruption of the cold chain cannot be excluded in many cases, which can significantly reduce the duration of the storage life, reserves for which it cannot be safely determined whether the cold chain has been maintained uninterrupted are likely also discarded for safety reasons even before the expiration date is reached. It may also be the case that the blood donors carry germs or negative factors which were not visible or measurable at the time of the blood donation.

An objective quality control is desired. According to the corresponding guidelines, at least $2 \cdot 10^{11}$ thrombocytes and less than 1 million leukocytes or 3 million residual erythrocytes should be contained for example in a thrombocyte concentrate. The pH value of a thrombocyte concentrate should be between 6.4 and 7.8. The product must be sterile until the end of the maximum storage life.

Compliance with these guidelines can be quantitatively verified. To this end, counts of the thrombocytes, erythrocytes and leukocytes can for example be carried out in processes using microscopes.

Conventional methods for the quantitative quality controlling of blood-based products, in which for example the thrombocyte count, the erythrocyte count, the protein content, the pH value and/or the calcium content is determined, are time-consuming and expensive, in particular because these samples may no longer be used for transfusion. According to the hemotherapy directive of the German Medical Association (as of 2010), 1% of all blood-based products, but at least 4 bags must be withheld for quality controlling. A proportion of $0.4 \cdot \sqrt{n}$ of the products must be verified when verifying the sterility and is thus also not suitable for use.

Furthermore, conventional methods provide no information or only very limited information regarding the functionality of the cells contained in the blood-based product. The functionality state or the storage life duration of the blood-based products could also be connected to the condition or state of the donor. Donor-specific possibilities for quality testing are not known at present.

SUMMARY OF THE INVENTION

The object of the invention is to indicate methods and devices which enable an objective verification of blood. In particular, the object underlying the exemplary embodiments is to indicate methods and devices which enable an objective verification of blood-based products. Blood-based products are here in particular understood as bags with an erythrocyte concentrate, bags with thrombocyte concentrate, bags with granulocyte concentrate, bags with leukocyte concentrate, whole blood reserves or blood plasma reserves.

Methods and devices are indicated herein. The method is provided for quality controlling a blood-based product, which comprises an erythrocyte concentrate, a thrombocyte concentrate, a granulocyte concentrate, a leukocyte concentrate, whole blood or blood plasma, wherein the method comprises: recording a Raman spectrum by means of Raman spectroscopy of a sample of the blood-based product, and determining whether the blood-based product can be used for a transfusion by means of evaluating the Raman spectrum. By means of evaluating the Raman spectrum, a functional modification of cells of at least one cell type of the blood-based product is identified in order to determine whether the blood-based product can be used or a transfusion, wherein the cell type is selected from a group consisting of erythrocytes, thrombocytes, granulocytes and leukocytes. By means of evaluating the Raman spectrum, it is quantitatively determined which proportion of the cells of at least one cell type is subject to a functional modification. In order to quantitatively determine which proportion of the cells of at least one cell type is subject to the functional modification, a plurality of recorded Raman spectra are respectively subjected to a principal component analysis. By means of evaluating the Raman spectrum, the presence of bacteria or other impurities in the blood-based product is identified in order to determine whether the blood-based product can be used for a transfusion. The evaluation of the Raman spectrum comprises a spectral analysis of the Raman spectrum. The recording of the Raman spectrum comprises collecting at least one cell of the sample in an optical trap in order to record the Raman spectrum. The optical trap is produced by means of an excitation beam of a Raman spectroscopy system. In the aforementioned methods, the at least one cell is selected from a group consisting of erythrocytes, thrombocytes, granulocytes and leukocytes. In accordance with an aspect of the disclosed method, there is also disclosed a device for quality controlling a blood-based product which comprises an erythrocyte concentrate, a thrombocyte concentrate, a granulocyte concentrate, a leukocyte concentrate, whole blood and/or blood plasma, wherein the device comprises a Raman spectroscopy system in order to record a Raman spectrum of a sample of the blood-based product), and an evaluation device which is coupled to the Raman spectroscopy system and which is configured to determine by means of the recorded Raman spectrum whether the blood-based product can be used for a transfusion. The evaluation device for performing a cluster analysis, in particular a principal component analysis, is configured to identify functional modification of cells of at least one cell type of the blood-based product, wherein the cell type is selected from a group consisting of erythrocytes, thrombocytes, granulocytes and leukocytes. The evaluation device is configured to quantitatively determine by means of the cluster analysis which proportion of the cells of the at least one cell type is subject to a functional modification and is used to perform the method disclosed above. In accordance with another aspect of the invention, the disclosed device is used to identify a contamination, a disease or a progression of disease, and wherein the device comprises a Raman spectroscopy system in order to record at least one Raman spectrum of at least one blood sample, and an evaluation device which is coupled to the Raman spectroscopy system and which is configured to automatically identify a disease or a progression of disease by means of the recorded at least one Raman spectrum. The disease that may be identified by the disclosed device is selected from a group consisting of tumour diseases, blood coagulation disorders and thrombosis.

In the case of a method for quality controlling a blood-based product, which comprises an erythrocyte concentrate, a thrombocyte concentrate, a granulocyte concentrate, a leukocyte concentrate, whole blood and/or blood plasma, a Raman spectrum is recorded by means of Raman spectroscopy of a sample of the blood-based product. By means of evaluating the Raman spectrum, it is determined whether the blood-based product can be used for a transfusion.

When recording the Raman spectrum of a sample, the fluid itself can be measured (for example the calcium content and/or protein content). The cellular components such as erythrocytes, leukocytes, granulocytes or thrombocytes can, however, also be identified and examined with regard to their functionality. These cellular components can be collected individually or in a group with a few cells in an optical trap and measured by recording the Raman spectrum. The Raman spectrum can also be recorded for a sample which is a microdroplet or the Raman spectrum can be recorded for a sample which is the dried residue of a droplet after evaporation. The sample can also be a pellet which is produced by means of centrifugation and for which the Raman spectrum is recoded.

The use of Raman spectroscopy enables not only verification of whether the relevant cell types are present, but also a determination of the biological functionality. In particular, it can be determined whether and, optionally, which proportion of erythrocytes, leukocytes, granulocytes or thrombocytes is subject to a molecular modification. An example of such a molecular modification is cell death (apoptosis or necrosis). Modifications of the composition or the quantity ratios and concentration of the biomolecules in the cells can also be identified by means of evaluating the Raman spectrum, said modifications restrict functionality of the cell. As a result, conclusions can be drawn regarding the usability and functionality of the blood-based product.

The use of Raman spectroscopy also enables a determination of whether germs or bacteria are present in the reserve. Infected cells, e.g. infected erythrocytes may also be identified, for example in the case of malaria. Furthermore, the types of impurities of the reserve can also be determined from the Raman spectrum and/or the number of impurities can be estimated.

The evaluation can take place automatically by means of an evaluation device. The evaluation device may be a computer. The evaluation device may comprise one or a plurality of processors or controllers. The evaluation device can generate an optical and/or acoustic output as a result of the evaluation which shows whether the blood-based product can still be used for a transfusion. The evaluation device can output information regarding the state of cellular components of the blood-based product and/or information regarding impurities contained in the blood-based product as a result of the evaluation.

In the case of evaluating the Raman spectrum, a spectral analysis of the Raman spectrum can be carried out.

By evaluating the Raman spectrum, an erythrocyte decay or a thrombocyte decay, an erythrocyte cell death or a thrombocyte cell death or another functional modification of a cellular component of the blood-based product can be identified. By evaluating the Raman spectrum, a restriction of the functionality of erythrocytes, thrombocytes, granulocytes or leukocytes can be identified.

In order to identify which proportion of cells of a cell type, e.g. which proportion of erythrocytes, thrombocytes, granulocytes or leukocytes is subject to a functional modification, which makes the blood-based product unsuitable for a transfusion, a cluster analysis of a plurality of Raman spectra of cells of this cell type can automatically be performed. The cluster analysis can be a principal component analysis. By means of the cluster analysis, it can be quantitatively identified whether cells have to be assigned to a cluster of intact cells or to another cluster of functionally impaired cells. The number of cells in the different clusters provides information regarding which proportion of cells of the cell type is subject to the functional modification.

For blood-based products, which comprise a plurality of different cellular components of the blood, a cluster analysis can distinguish not only between intact cells and functionally modified cells, but also between different cell types.

An assignment to different cell types can take place for a cluster analysis or for a different analysis of the recorded Raman spectra for example by means of different wavenumber ranges. In order to identify thrombocytes and/or in order to identify functional modifications of thrombocytes, at least one wavenumber in the wavenumber range of 1296 $cm^{-1}$ to 1333 $cm^{-1}$ can for example be evaluated in order to determine whether the blood-based product can be used for a transfusion.

In order to identify erythrocytes and/or in order to identify functional modifications of erythrocytes, at least one wavenumber from one or a plurality of wavenumber ranges of 1650 to 1600 $cm^{-1}$, from 1350 to 1250 $cm^{-1}$, from 1180 $cm^{-1}$ to 1120 $cm^{-1}$, from 1100 $cm^{-1}$ to 1050 $cm^{-1}$, from 930 $cm^{-1}$ to 890 $cm^{-1}$ or from 700 $cm^{-1}$ to 650 $cm^{-1}$ can for example be evaluated in order to determine whether the blood-based product can be used for a transfusion.

In order to perform the cluster analysis, the mentioned wavenumber ranges do not necessarily have to be evaluated, but rather other principal components can also be evaluated.

In the case of evaluating the Raman spectrum, one or a plurality of Raman peaks can be identified and can optionally be further evaluated, which are assigned to red blood cells. The Raman spectrum can be evaluated in the case of at least one and optionally in the case of a plurality of wavenumbers which are selected from the group consisting of 669 $cm^{-1}$, 750 $cm^{-1}$, 752 $cm^{-1}$, 999 $cm^{-1}$, 1122 $cm^{-1}$, 1210 $cm^{-1}$, 1444 $cm^{-1}$, 1543 $cm^{-1}$ and 1617 $cm^{-1}$.

In the case of evaluating the Raman spectrum, a Raman peak can for example be identified, which is assigned to guanine. A spectral weight or a width of the Raman peak, which is assigned to guanine, can be determined.

Alternatively or additionally, in the case of evaluating the Raman spectrum, a Raman peak can for example be identified, which is assigned to deoxyribonucleic acid. A spectral weight or a width of the Raman peak, which is assigned to deoxyribonucleic acid, can be determined The Raman peak may be an amide-III-band or a a-Helix.

Alternatively or additionally, in the case of evaluating the Raman spectrum, a Raman peak can for example be identified, which is assigned an erythrocyte decay, an erythrocyte cell death or to a different functional impairment of erythrocytes. A spectral weight or a width of the Raman peak, which is assigned to an erythrocyte cell death, can be determined.

Alternatively or additionally, in the case evaluating the Raman spectrum, a Raman peak can for example be identified, which is assigned a thrombocyte decay, to a thrombocyte cell death or to a different functional impairment of thrombocytes. A spectral weight or a width of the Raman peak, which is assigned to a thrombocyte cell death, can be determined.

In order to identify one or a plurality of the mentioned Raman peaks, the Raman spectrum can be evaluated in a predefined wavenumber range. For example, the Raman spectrum can be evaluated in a wavenumber range of 1296 cm$^{-1}$ to 1333 cm$^{-1}$ in order to determine whether the blood-based product can be used for a transfusion.

The Raman spectrum can undergo a spectral analysis. For example, an analysis of mean value spectra, a principal component analysis and/or a support vector machine (SVM) can be used in order to determine whether the blood-based product can be used for a transfusion.

In order to record the Raman spectrum, at least one cell of the sample can be collected in an optical trap. In this manner, cells, which are in solution, can also be recorded in a spectroscopic manner. In the case of further cells, for example cells which are on an objective slide base, it is not absolutely necessary to collect the cells in an optical trap.

A non-focussed beam can be used for measuring a Raman spectrum if the sample has the form of a dried droplet or pellet, but also in order to determine a broad spectrum directly in an amount of fluid. To this end, light conductor-based Raman spectroscopy systems or a Raman spectroscopy system, which is not optimally focused through an objective, can for example be used since such systems usually measure in a planar manner, wherein the covered dimensions can reach up into the millimeter range.

In order to record the Raman spectrum, at least one optical light conductor, for example an optical fibre, can be used in order to direct the excitation beam and/or the scattered light.

The optical trap can be produced by an excitation beam of Raman spectroscopy. In this manner, a Raman signal can be maintained with a good signal-noise ratio using simple means.

The excitation beam can have a wavelength of between 700 and 1064 nm.

The at least one cell can be selected from a group consisting of erythrocytes, thrombocytes and leukocytes. The at least one cell can be a granulocyte.

A functionality of erythrocytes and/or thrombocytes can be evaluated by Raman spectroscopy. Additionally or alternatively, it can be quantitatively recorded by Raman spectroscopy whether and, where appropriate what quantity of impurities are contained in the blood-based product.

In order to identify bacteria and germs, a quantity of blood-based product can for example be removed from the reserve and further processed. The quantity of blood-based product can be further processed in order to concentrate any impurities present. In order to concentrate the impurities, the cellular proportions such as erythrocytes and/or thrombocytes and/or leukocytes can for example be separated at least in part before the sample is further concentrated, for example by a combination with hydrogel. The sample can be examined by Raman spectroscopy in order to verify the sterility and thus the usability of the blood-based product.

The sample can be removed from the blood-based product in order to perform the Raman spectroscopy. The blood-based product can comprise a plastic bag, in which an erythrocyte concentrate, a thrombocyte concentrate, a granulocyte concentrate, a leukocyte concentrate or whole blood can be contained. The sample can be removed from the blood-based product by hand using a syringe or automatically by a robot.

The Raman spectroscopy can be performed while the blood-based product is contained in the bag. The reserve is still available as a sterile reserve after the quality controlling. The blood-based product can be contained in a bag which is designed for use in a Raman spectroscopy system. The bag can consist of a material which has high transmissivity for the excitation beam and the Raman scattered light of the relevant biological objects (for example erythrocytes, thrombocytes, bacteria and/or germs). The bag can comprise a window made of a material which has high transmissivity for the excitation beam and the Raman scattered light of the relevant biological objects (for example erythrocytes, thrombocytes, leukocytes, bacteria and/or germs).

A device for quality controlling a blood-based product, which contains an erythrocyte concentrate, a thrombocyte concentrate, a granulocyte concentrate, a leukocyte concentrate, whole blood and/or blood plasma, comprises a Raman spectroscopy system for recording a Raman spectrum of a sample of the blood-based product. The device comprises an evaluation device which is coupled to the Raman spectrometer and which is configured to determine by means of the recorded Raman spectrum whether the blood-based product can be used for a transfusion.

The evaluation device can be a computer. The evaluation device can comprise one or a plurality of processors or controllers. The evaluation device can produce an optical and/or acoustic output as a result of the evaluation which shows whether the blood-based product can be used for a transfusion.

The evaluation device can be coupled to an image sensor of the Raman spectroscopy system. The image sensor can be a CCD sensor or a CMOS sensor.

In order to identify which proportion of cells of a cell type, e.g. which proportion of erythrocytes, thrombocytes, granulocytes or leukocytes is subject to a functional modification, which makes the blood-based product unsuitable for a transfusion, the evaluation device can be configured to perform a cluster analysis of a plurality of Raman spectra of cells of this cell type. The cluster analysis can be a principal component analysis. The evaluation device can be configured to quantitatively identify by means of the cluster analysis whether cells have to be assigned to a cluster of intact cells or to another cluster of functionally impaired cells. The number of cells in the different clusters can be determined by the evaluation device in order to determine which proportion of cells of the cell type is subject to the functional modification.

For blood-based products, which comprise a plurality of different cellular components of the blood, the evaluation device, by means of a cluster analysis, can distinguish not only between intact cells and functionally modified cells, but also between different cell types.

An assignment to different cell types by means of the evaluation device can take place in the case of a cluster analysis or in the case of a different analysis of the recorded Raman spectra for example by means of different wavenumber ranges. In order to identify thrombocytes and/or in order to identify functional modifications of thrombocytes, at least one wavenumber in the wavenumber range of 1296 cm$^{-1}$ to 1333 cm$^{-1}$ can for example be evaluated by means of the evaluation device in order to determine whether the blood-based product can be used for a transfusion.

In order to identify erythrocytes and/or in order to identify functional modifications of erythrocytes, at least one wavenumber from one or a plurality of wavenumber ranges of 1650 to 1600 cm$^{-1}$, from 1350 to 1250 cm$^{-1}$, from 1180 cm$^{-1}$ to 1120 cm$^{-1}$, from 1100 cm$^{-1}$ to 1050 cm$^{-1}$, from 930 cm$^{-1}$ to 890 cm$^{-1}$ or from 700 cm$^{-1}$ to 650 cm$^{-1}$ can for example be evaluated in order to determine whether the blood-based product can be used for a transfusion.

In order to perform the cluster analysis by means of the evaluation device, the mentioned wavenumber ranges do not necessarily have to be evaluated, but rather other principal components can also be evaluated.

The evaluation device can be configured to identify a Raman peak which is assigned to a thrombocyte cell death in order to determine whether the reserve can be used for a transfusion. The evaluation device can be configured to identify a Raman peak which represents a modification of the composition of the biomolecules in the cell which restricts the functionality of the cell.

The evaluation device can be configured to identify and further evaluate a Raman peak which is assigned to the red blood cells.

The evaluation device can be configured to carry out a spectral analysis of the Raman spectrum.

The Raman spectroscopy system can comprise a laser for producing an excitation beam for the Raman spectroscopy. The laser can produce light with a wavelength of between 700 nm and 1064 nm.

The Raman spectroscopy system can comprise optical components in order to produce an optical trap by means of the excitation beam in which at least one cell of the sample can be collected in order to record the Raman spectrum. The optical components can comprise a lens. The optical components can comprise a light conductor in which the excitation beam for the Raman spectroscopy is directed. By means of collection in an optical trap, in particular cells, which are movable, can also be subjected to the Raman spectroscopy. In the case of a Raman spectroscopy on dried droplets or pellets, the production of an optical trap is not necessarily required.

The device can be configured to automatically perform the method according to an exemplary embodiment.

According to further exemplary embodiments, the devices and methods can be used in order to automatically identify diseases and progressions of disease.

A device according to a further exemplary embodiment is configured to identify a disease or a progression of disease and comprises a Raman spectroscopy system for recording at least one Raman spectrum of at least one blood sample and an evaluation device which is coupled to the Raman spectroscopy system and which is configured to evaluate the Raman spectrum in order to identify a disease or a progression of disease.

The device can be configured to identify disease or a progression of a disease by means of evaluating the Raman spectrum which is selected from a group consisting of tumour diseases, blood coagulation disorders and thrombosis.

The device can be configured to identify and evaluate Raman peaks, which are assigned to erythrocytes, in one or a plurality of Raman spectra in order to identify the disease or the progression of disease.

The evaluation device can be configured to objectively and quantitatively examine the blood-based product by means of evaluating one or a plurality of Raman spectra. A comparison with reference spectra stored in a database can be carried out in order to determine which cell types are present and/or in order to quantify the number of cells of one or a plurality of cell types and/or in order to identify functional modifications of cells of one or a plurality of cell types. Alternatively or additionally, processing of the Raman spectra can be carried out, for example by means of a cluster analysis in order to identify different cell types. A comparison with reference spectra stored in a database can be carried out in order to identify bacteria, germs or other impurities.

The evaluation device can be configured to store recorded Raman spectra of the blood-based product in a non-volatile manner in a memory.

The evaluation device can comprise a memory in which information regarding the position of Raman peaks of different cell types of a blood-based product are stored. Information regarding the position of Raman peaks of erythrocytes can be stored in the memory. Alternatively or additionally, information regarding the position of Raman peaks of thrombocytes can be stored in the memory. Alternatively or additionally, information regarding the position of Raman peaks of granulocytes can be stored in the memory. Alternatively or additionally, information regarding the position of Raman peaks of leukocytes can be stored in the memory. The information regarding the position of the Raman peaks can be stored in a different manner. For example, the relevant wavenumber ranges for fresh cells and for functionally modified cells can be stored. Information regarding ranges of multi-dimensional spaces of a cluster analysis, in which the spectra are respectively arranged, can be stored.

A method for identifying a contamination, a disease or a progression of disease according to a further exemplary embodiment comprises recording at least one Raman spectrum of at least one blood sample and an evaluation device which is coupled to the Raman spectroscopy system and which is configured to evaluate the Raman spectrum in order to identify a disease or a progression of disease.

The method can be performed automatically using the device according to an exemplary embodiment.

The obtainment of the blood sample is not part of the claimed method.

BRIEF DESCRIPTION OF THE FIGURES

The invention is explained further by means of preferred exemplary embodiments below with reference to the drawing.

DESCRIPTION OF EXEMPLARY EMBODIMENTS

The features of the different described embodiments can be combined with each other, insofar as this is not expressly excluded in the description below.

Devices and methods according to exemplary embodiments can be used for quality controlling blood-based products. The term "blood-based product" here includes reserves with erythrocyte concentrate, reserves with thrombocyte concentrate, reserves with granulocyte concentrate, reserves with leukocyte concentrate, reserves with whole blood and reserves with blood plasma. Granulocyte concentrates also contain other leukocytes in addition to granulocytes which can cause a GvHD (graft versus host) reaction in the recipient. The reproductive capability of the lymphocytes is irreversibly impaired by means of irradiation. A leukocyte concentrate is obtained by means of leukopheresis from donor blood and in particular contains granulocytes. The leukocyte concentrate is maintainable only for a few hours and is administered for infection prophylaxis in the case of pronounced, but reversible leukocyte deficiency.

In the case of devices and methods according to exemplary embodiments, a Raman spectrum of a sample of the blood-based product is recorded. The Raman spectrum is evaluated in order to determine whether the blood-based product is still suitable for a transfusion. The blood-based product can be a blood reserve, wherein for example an erythrocyte concentrate, a thrombocyte concentrate, a granulocyte concentrate, a leukocyte concentrate, whole blood or blood plasma is contained in a suitable container.

Figure 1:
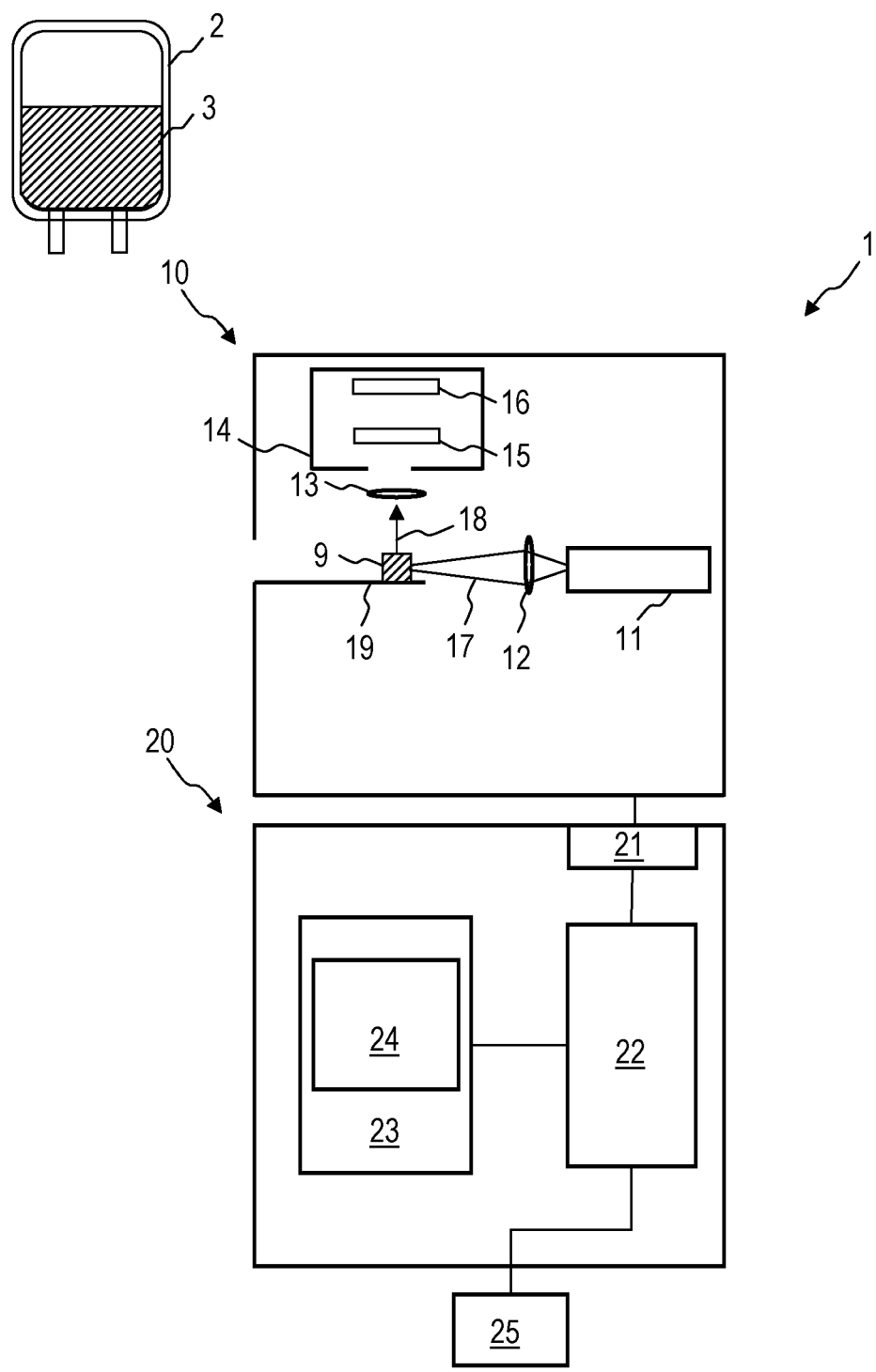
FIG. 1 shows a schematic illustration of a device according to an exemplary embodiment.

FIG. 1 is a schematic illustration of a device 1 according to an exemplary embodiment. The device 1 is configured to determine whether a blood reserve 2 is suitable for a transfusion. The corresponding determination takes place by means of a Raman spectrum which the device 1 records and can automatically evaluate. A sample of a blood-based product 3, which may for example be an erythrocyte concentrate, a thrombocyte concentrate, a granulocyte concentrate, a leukocyte concentrate, whole blood or blood plasma, is used for a Raman spectroscopy in order to determine whether the blood-based product 3 may be used for a transfusion. The manufacture of the blood reserve 2, which can be carried out according to conventional techniques, is not subject matter of the methods and devices disclosed here.

The device 1 comprises a Raman spectroscopy system 10 and an evaluation device 20. The Raman spectroscopy system 10 is configured to record a Raman spectrum of a sample 9 of the blood-based product 3. A quantity of the blood-based product 3 can be removed from the blood reserve 2 and after further processing can be prepared as a sample 9 for the Raman spectroscopy system 10. The sample 9 can contain blood cells which are movable in a solution. The sample 9 can contain dried blood or a pellet which is produced from the blood-based product 3.

In the case of further designs, the Raman spectroscopy system 10 can also be designed such that the Raman spectrum is recorded directly on the blood reserve 2 without a quantity of the blood-based product 3 having to be first removed from said blood reserve. An entire blood reserve can then be inserted into the Raman spectroscopy system.

The Raman spectroscopy system 10 comprises a light source 11 which can in particular be a laser. The light source 11 is configured to output an excitation beam 17. The excitation beam 17 can for example have a wavelength in the range between 700 nm and 1064 nm, e.g. approximately 785 nm. A Raman spectrometer 14 receives light 18 scattered on the sample 9 by Stokes processes and/or Anti-Stokes processes. The Raman spectrometer 14 can comprise a diffractive element 15 and an image sensor 16 in order to record the Raman spectrum of the sample 9. The Raman spectroscopy system 10 can comprise further elements in a manner known per se, for example focussing optical elements 12, 13, which can be designed as lenses, and/or diaphragms.

Then device 1 comprises an evaluation device 20. The evaluation device 20 can be a computer or can comprise a computer. The evaluation device 20 is coupled to the Raman spectroscopy system 10. The evaluation device 20 can control the recording of the Raman spectrum by the Raman spectroscopy system 10.

The evaluation device 20 comprises an interface 21 in order to receive data from the image sensor 16 of the Raman spectroscopy system 10. The evaluation device comprises an integrated semi-conductor circuit 22 which can comprise a processor or controller and which is configured to evaluate the recorded Raman spectrum in order to determine [Translator—end of sentence is missing]. The integrated semi-conductor circuit 22 is configured to determine by means of the Raman spectrum whether the blood reserve 2 can still be used for a transfusion. The integrated semi-conductor circuit 22 can be configured in particular in order to determine by means of evaluating the Raman spectrum whether and to what extent the functionality of the cells is impaired. The integrated semi-conductor circuit 22 can be configured to determine by means of evaluating the Raman spectrum whether a cell death of erythrocytes and/or thrombocytes and/or granulocytes and/or leukocytes has occurred. The integrated semi-conductor circuit 22 can be configured to determine by means of evaluating the Raman spectrum whether biological molecules of the cells are present, which impair the function of the cell.

As is described in detail with reference to FIG. 2 to FIG. 11, the integrated semi-conductor circuit 22 can be configured to identify the presence or absence of determined Raman peaks or to determine the spectral weight of Raman peaks which relate to the quality of the blood reserve 2. For example, the integrated semi-conductor circuit 22 can identify and/or further evaluate Raman peaks, which are assigned to red blood cells or which are assigned to a cell death of erythrocytes and/or thrombocytes, granulocytes, leukocytes. The integrated semi-conductor circuit 22 can be configured to evaluate for example the Raman spectrum in at least one predefined wavenumber range, e.g. the Raman spectrum in the wavenumber range between 1296 $cm^{-1}$ and 1333 $cm^{-1}$ in order to determine whether the blood-based product 3 can be used for a transfusion.

The integrated semi-conductor circuit 22 can be configured to automatically verify the sterility of the blood reserve 2 by analysing the Raman spectrum. The integrated semi-conductor circuit 22 can be configured to identify one or a plurality of Raman peaks, which are assigned to impurities, for example bacteria or viruses, in order to determine whether the blood reserve 2 is sterile.

The evaluation device 20 can comprise a memory 23 in which comparative data 24 is stored which the integrated semi-conductor circuit 22 can use when evaluating the Raman spectrum.

Information regarding the position and/or the spectral weight of different Raman peaks for the different cell types of one or a plurality of blood-based products can be stored in a non-volatile manner in the memory 23 of the device 1. Alternatively or additionally, the information regarding the position and/or the spectral weight of different Raman peaks for the different blood-based products can be determined by the device 1 by means of methods of supervised learning or other machine learning techniques.

The evaluation device 20 can comprise an optical and/or acoustic output unit 25, via which the information dependent on the analysis of the Raman spectrum is output, which shows whether or not the blood reserve 2 can still be used. The output unit 25 can also be structurally integrated into a housing of the evaluation device 20 or of the Raman spectroscopy system 10.

Even though the evaluation device 20 and the Raman spectroscopy system 10 in FIG. 1 are schematically illustrated as separate units, the functions of the evaluation device 20 can also be integrated into a housing of the Raman spectroscopy system 10. The Raman spectroscopy system 10 and the evaluation device 20 can be designed as mobile, in particular portable units.

Figure 2:
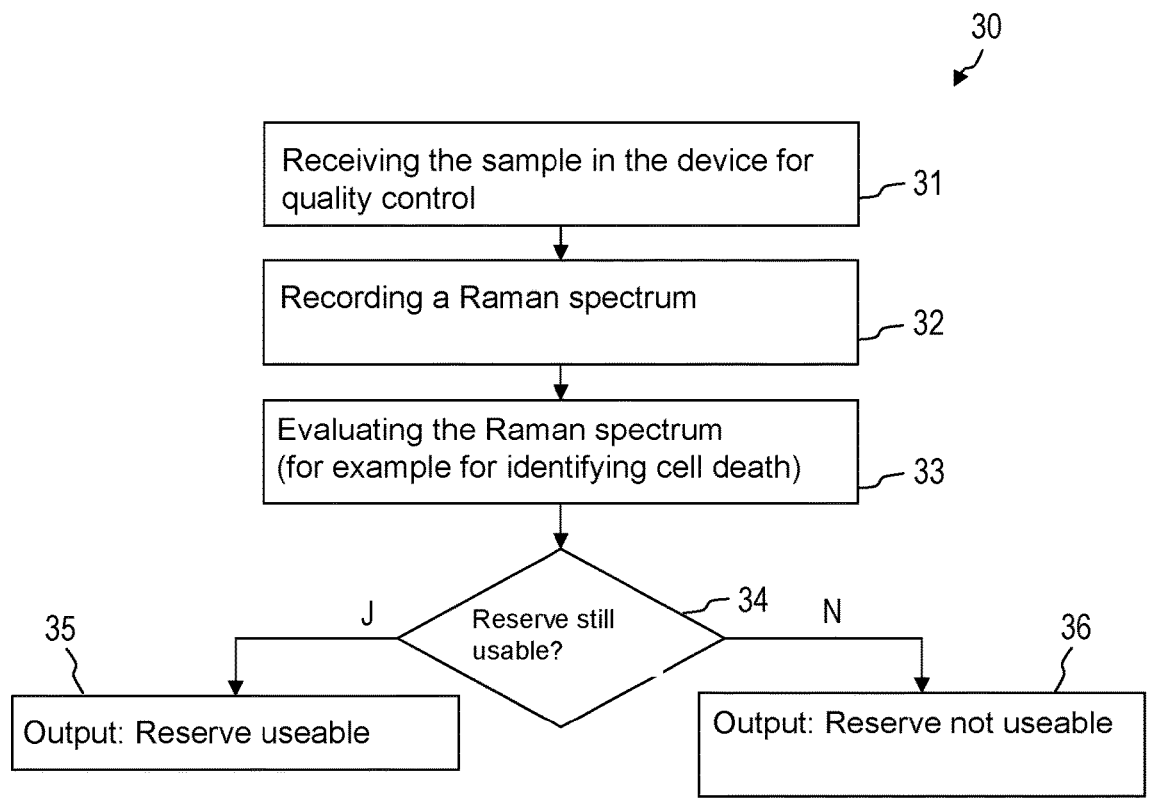
FIG. 2 is a flow diagram of a method according to an exemplary embodiment.

FIG. 2 is a flow diagram of a method 30. The method 30 can be performed fully automatically by the device 1 without intermediate operational actions of a user or it can be performed dependent on user inputs. A sample 9 can be obtained from the blood-based product 9. For example, a quantity of the blood-based product 3 can be removed from the blood reserve 2 using a syringe. The quantity of the blood-based product 3 removed can be thinned in order to produce the sample 9. More than one sample can also be produced and analysed using Raman spectroscopy. For example, impurities can be firstly concentrated from samples of blood-based product removed from the blood reserve 2, for example by separating erythrocytes and/or thrombocytes and producing conditions which lead to a reproduction of any impurities present in the removed sample.

In this manner, the quantitative determination of impurities can be improved for verifying the sterility. The sample 9 can also be present in solid form. For example, the removed quantity of the blood-based product 3 can be a droplet, which is firstly left to evaporate in order to use the material remaining after evaporation as the sample 9. The sample 9 can be a pellet.

In the case of step 31, the device 1 receives the sample 9. For example, a sample holder 19 can be automatically drawn in after the sample 9 has been placed there.

In the case of step 32, a Raman spectrum of the sample 9 is recorded. The light source 11 is controlled such that an excitation beam 17 is produced. The excitation beam 17 or a beam of electromagnetic radiation different from the excitation beam 17 can produce an optical trap in which cells of the sample 9 are collected for Raman spectroscopy, for example if the sample 9 is liquid.

A plurality of Raman spectra can also be recorded. For example, a plurality of Raman spectra can be recorded for the same sample or different samples in order to determine from a Raman spectrum whether the erythrocytes and/or thrombocytes and/or leukocytes are alive and in order to determine from a different Raman spectrum how many impurities the blood reserve contains.

In the case of step 33, the evaluation device 20 evaluates the recorded Raman spectrum. The evaluation device 20 can identify Raman peaks, which are for example assigned to guanine, deoxyribonucleic acid or to a cell death of erythrocytes or thrombocytes. The evaluation device 20 can identify Raman peaks which are assigned to red blood cells. The evaluation device 20 can carry out a static evaluation of the Raman spectrum, for example by means of a spectral analysis.

In the case of step 34, depending on the evaluation of the Raman spectrum, it is verified whether the blood reserve 2 with the blood-based product 3 may be used for a transfusion. To this end, the evaluation device 20 can for example compare a spectral weight of a Raman peak, which is assigned to the cell death of erythrocytes or thrombocytes, with a threshold value. Depending on whether the spectral weight of Raman peaks, which is associated with the cell death of erythrocytes or thrombocytes, is greater than the threshold value, it can be determined that the sample is no longer suitable for the transfusion. Alternatively or additionally, data points, which have been determined by a spectral analysis of the Raman spectrum, can be used in order to determine whether the blood reserve is already old or has been stored such that it can no longer be used for a transfusion. Alternatively or additionally, it can be determined by means of the analysis of the Raman spectrum whether the sample is still sterile. A type and a number of impurities can be estimated.

In the case of step 35 or step 36, an output unit is actuated such that information is indicated, which shows whether or not the blood reserve can still be used.

Figure 3:
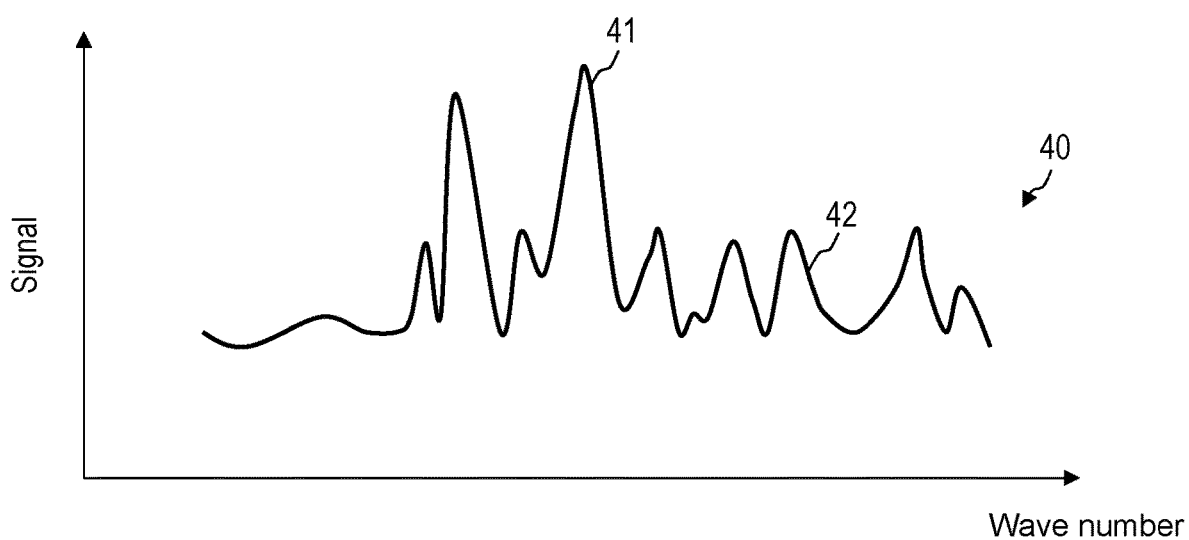
FIG. 3 shows a schematic illustration of a Raman spectrum which is evaluated by devices and methods according to exemplary embodiments.

FIG. 3 schematically shows a Raman spectrum 40 which is evaluated by the evaluation device 20. The Raman spectrum 40 can comprise a plurality of Raman peaks 41, 42 which can be automatically identified by the evaluation device 20 and which provide information regarding whether the blood reserve can still be used. The Raman peaks 41, 42 can for example be associated with substances which indicate a cell death (e.g. apoptosis) of erythrocytes or thrombocytes. The Raman peaks 41, 42 can be assigned to red blood cells. For example, one or a plurality of the analysed Raman peaks can be in wavenumbers which are selected from the group consisting of 669 $cm^{-1}$, 750 $cm^{-1}$, 752 $cm^{-1}$, 999 $cm^{-1}$, 1122 $cm^{-1}$, 1210 $cm^{-1}$, 1444 $cm^{-1}$, 1543 $cm^{-1}$ and 1617 $cm^{-1}$.

The evaluation device 20 can, in a targeted manner, analyse only a predefined wavenumber range or a plurality of predefined wavenumber ranges of the Raman spectrum 40 in order to determine whether the blood reserve is still suitable for a transfusion. The evaluation device 20 can for example analyse a wavenumber range of 1200 $cm^{-1}$ to 1400 $cm^{-1}$. The evaluation device 20 can for example analyse a wavenumber range of 1276 $cm^{-1}$ to 1333 $cm^{-1}$. Other wavenumber ranges can be used, for example wavenumber ranges in which there are characteristic Raman peaks of red blood cells.

Figure 4:
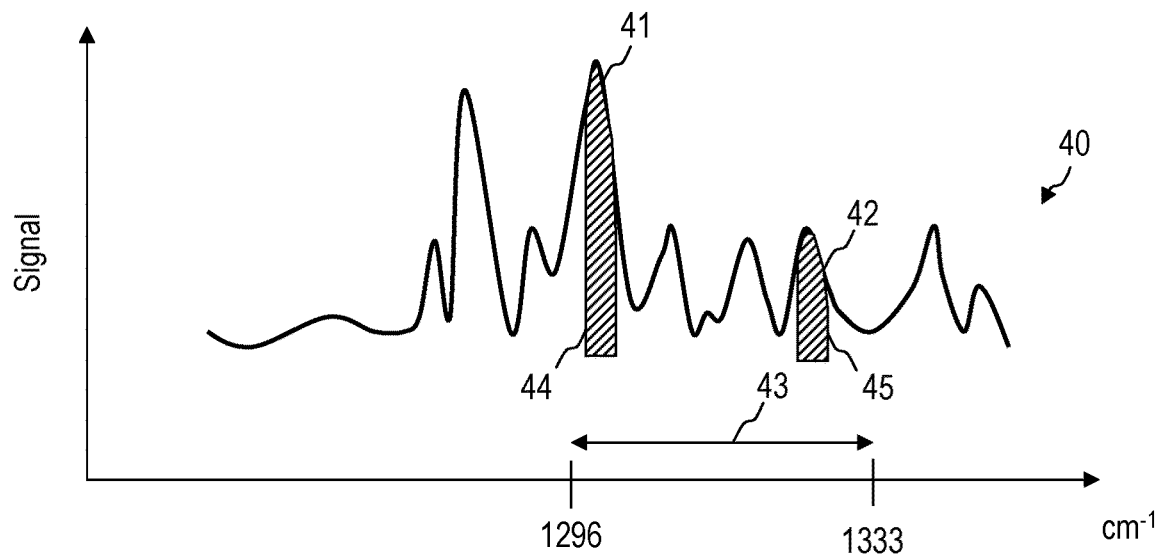
FIG. 4 shows a schematic illustration of a Raman spectrum which is evaluated by devices and methods according to exemplary embodiments.

FIG. 4 schematically shows the Raman spectrum 40 which is evaluated by the evaluation device 20. A wavenumber range of 1276 $cm^{-1}$ to 1333 $cm^{-1}$ is illustrated only as an example, in which there are one or a plurality of Raman peaks 41, 42, which are identified by the evaluation device 20. A further evaluation by a spectral analysis can take place. For example, the evaluation device 20 can determine an integral 44, 45 of the signal 40 for the respective Raman peaks 41, 42, e.g. by numeric integration or totaling the signal amounts in a plurality of discrete wavenumber bands in order to obtain a measure for the spectral weight of the Raman peaks 41, 42. Further evaluations can be carried out, for example by a principal component analysis of the Raman spectrum 40, by evaluating the mean value spectrum or by a SVM, without being limited thereto.

Figure 5:
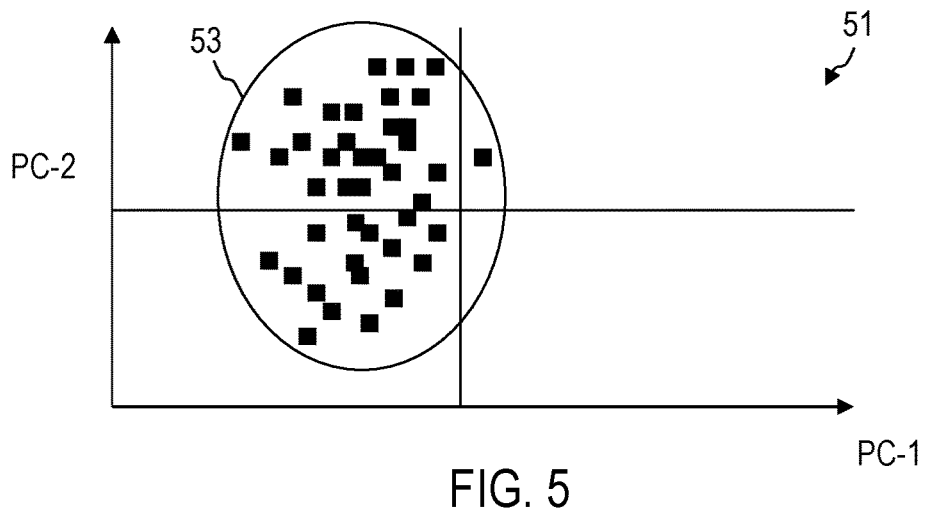
FIG. 5 shows a schematic illustration of a static evaluation of the Raman spectrum of a sample.
Figure 6:
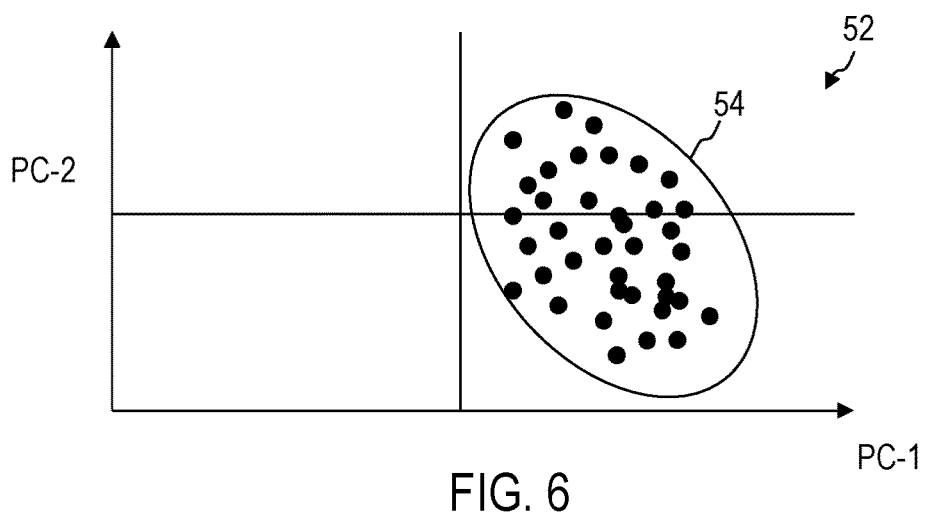
FIG. 6 shows a schematic illustration of a static evaluation of the Raman spectrum of a further sample.

FIG. 5 and FIG. 6 illustrate exemplary results of a principal component analysis or a different cluster analysis which is performed by the evaluation device 20 in order to determine whether the blood reserve is still suitable for a transfusion. In this connection, the principal component analysis is performed for a Raman spectrum or a plurality of Raman spectra which have been recorded from the sample 9. The data points are illustrated according to a pair of different principal components PC-1 and PC-2. FIG. 5 shows the data points 51 which have been obtained by processing the Raman spectrum of a relatively fresh blood reserve. FIG. 6 shows data points 52 which have been obtained by processing the Raman spectrum of a blood reserve which has been stored for longer and/or not at the correct temperature.

As can be discerned from a comparison of FIG. 5 and FIG. 6, the data points obtained by the principal component analysis are shifted depending on whether or not the blood reserve is still suitable for the transfusion. Accordingly, the evaluation device 20 can automatically determine by means of the principal component analysis of a Raman spectrum whether the respectively tested blood reserve 2 is still suitable for a transfusion.

Different regions 53, 54 can be defined in an N-dimensional space in which the points of the cluster analysis are arranged depending on whether cellular components of the blood-based product are intact cells or functionally impaired cells.

The data points, assigned to fresh and thus intact cellular components, can be arranged in a region 53. The data points, assigned to old and functionally modified cellular components, can be arranged in a region 54 of the N-dimensional space different therefrom. The dimension N of the space in which the cluster analysis is performed can be greater than two, in particular many times greater than two.

In order to identify which proportion of cells of a cell type, e.g. which proportion of erythrocytes, thrombocytes, granulocytes or leukocytes is subject to a functional modification, which makes the blood-based product unsuitable for a transfusion, the evaluation device 20 can thus be configured to perform a cluster analysis of a plurality of Raman spectra of cells of this cell type. The cluster analysis can be a principal component analysis. The evaluation device 20 can be configured to quantitatively identify by means of the cluster analysis whether cells have to be assigned to a cluster 51 of intact cells or to a different cluster 52 of functionally impaired cells. The number of cells in the different clusters 51, 52 can be determined by the evaluation device 20 in order to determine which proportion of cells of the cell type is subject to the functional modification.

For blood-based products, which comprise a plurality of different cellular components of the blood, the evaluation device 20, by means of a cluster analysis, can distinguish not only between intact cells and functionally modified cells, but also between different cell types. For each of the plurality of different cells types, it can then be determined which proportion of cells of this cell type is subject to a functional modification.

Figure 7:
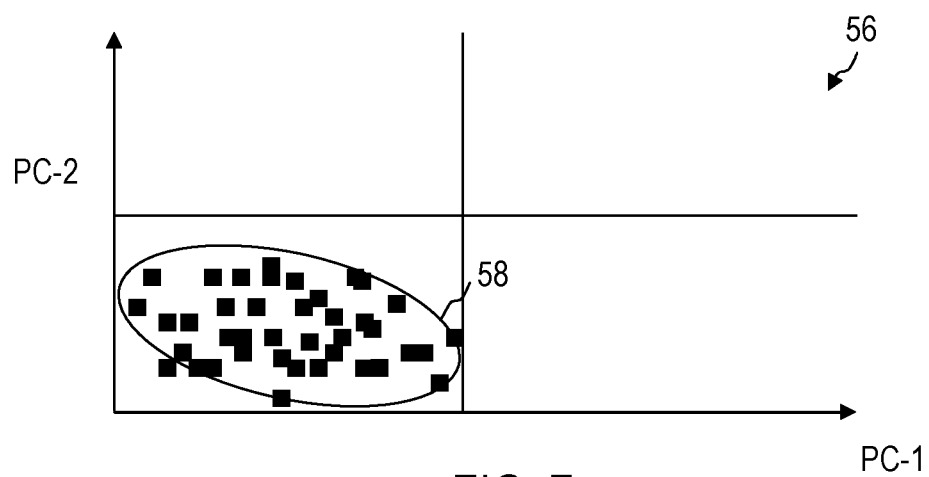
FIG. 7 shows a schematic illustration of a static evaluation of the Raman spectrum of a sample.
Figure 8:
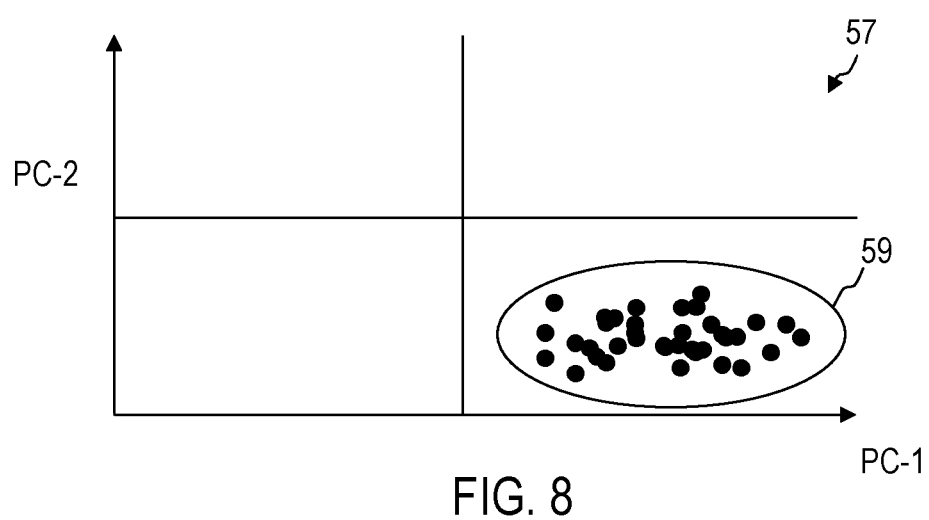
FIG. 8 shows a schematic illustration of a static evaluation of the Raman spectrum of a further sample.

FIG. 7 and FIG. 8 show the results of a cluster analysis, e.g. of a principal component analysis for a further cell type which is different from the further cell types examined in FIG. 5 and FIG. 6. FIG. 7 and FIG. 8 show, by way of example, results for erythrocytes in comparison with exemplary results for thrombocytes like those illustrated in FIG. 5 and FIG. 6. FIG. 7 and FIG. 8 show arrangements of data points, of which each is assigned to a Raman spectrum in an N-dimensional data space in the case of a principal component analysis. Other techniques of the cluster analysis can be used. FIG. 7 shows, by way of example, data points for Raman spectra of fresh intact cells. FIG. 8 shows, by way of example, data points for Raman spectra of old, functionally modified cells. As explained with reference to FIG. 5 and FIG. 6, by means of the cluster analysis, a distinction can be made between data 56, which can be assigned to intact cells, and data 57, which can be assigned to functionally modified cells.

Data points, which belong to cells of different cell types, are also in different regions of the data space in the case of the cluster analysis. Different cells can thus be distinguished. An assignment of data points to cellular components such as erythrocytes, thrombocytes, granulocytes or leukocytes can take place by a comparison with the position of data points assigned to intact cells. Such reference data can be stored in a non-volatile manner in the device 1.

As is illustrated by way of example in FIG. 7 in comparison to FIG. 5, the region 58, in which there are data points for cells of a second cell type in the case of the cluster analysis, differs from the region 53, in which there are data points for cells of a second cell type in the case of the cluster analysis.

Functional modifications of the cells, e.g. due to age or storage conditions of the blood-based product, lead to a shifting of the data points in the case of the cluster analysis from the region 58 into a region 59 different therefrom.

The evaluation device 20 can carry out an assignment to different cell types for example by means of different wavenumber ranges in the case of a cluster analysis or in the case of a different analysis of the recorded Raman spectra, in which wavenumber ranges the Raman spectra for cells of different cell types respectively comprise a characteristic behaviour. In order to identify thrombocytes and/or in order to identify functional modifications of thrombocytes, at least one wavenumber in the wavenumber range of 1296 $cm^{-1}$ to 1333 $cm^{-1}$ can for example be evaluated by means of the evaluation device 20 in order to determine whether the blood-based product can be used for a transfusion.

In order to identify erythrocytes and/or in order to identify functional modifications of erythrocytes by means of the evaluating device 20, at least one wavenumber from one or a plurality of wavenumber regions from 1650 to 1600 $cm^{-1}$, from 1350 to 1250 $cm^{-1}$, from 1180 $cm^{-1}$ to 1120 $cm^{-1}$, from 1100 $cm^{-1}$ to 1050 $cm^{-1}$, from 930 $cm^{-1}$ to 890 $cm^{-1}$ or from 700 $cm^{-1}$ to 650 $cm^{-1}$ can for example be evaluated in order to determine whether the blood-based product can be used for a transfusion.

Depending on the proportion of cells of one or a plurality of cell types, which are subject to a functional modification, the evaluation device 20 can automatically determine whether the blood-based product is suitable for a transfusion.

A threshold value for a cell type of the blood-based product can be stored in a non-volatile manner in the device 1. If the proportion of cells of the cell type, which are functionally impaired after the result of the principal component analysis or a different cluster analysis, exceeds the threshold value, the evaluation device 20 automatically identifies that the blood-based product is not suitable for the transfusion.

A further threshold value for a further cell type of the blood-based product can be stored in a non-volatile manner in the device 1. If the proportion of cells of the further cell type, which are functionally impaired after the result of the principal component analysis or a different cluster analysis, exceeds the further threshold value, the evaluation device 20 automatically identifies that the blood-based product is not suitable for the transfusion.

The cell type and the further cell type can both be selected from a group consisting of erythrocytes, thrombocytes, granulocytes and leukocytes.

Figure 9:
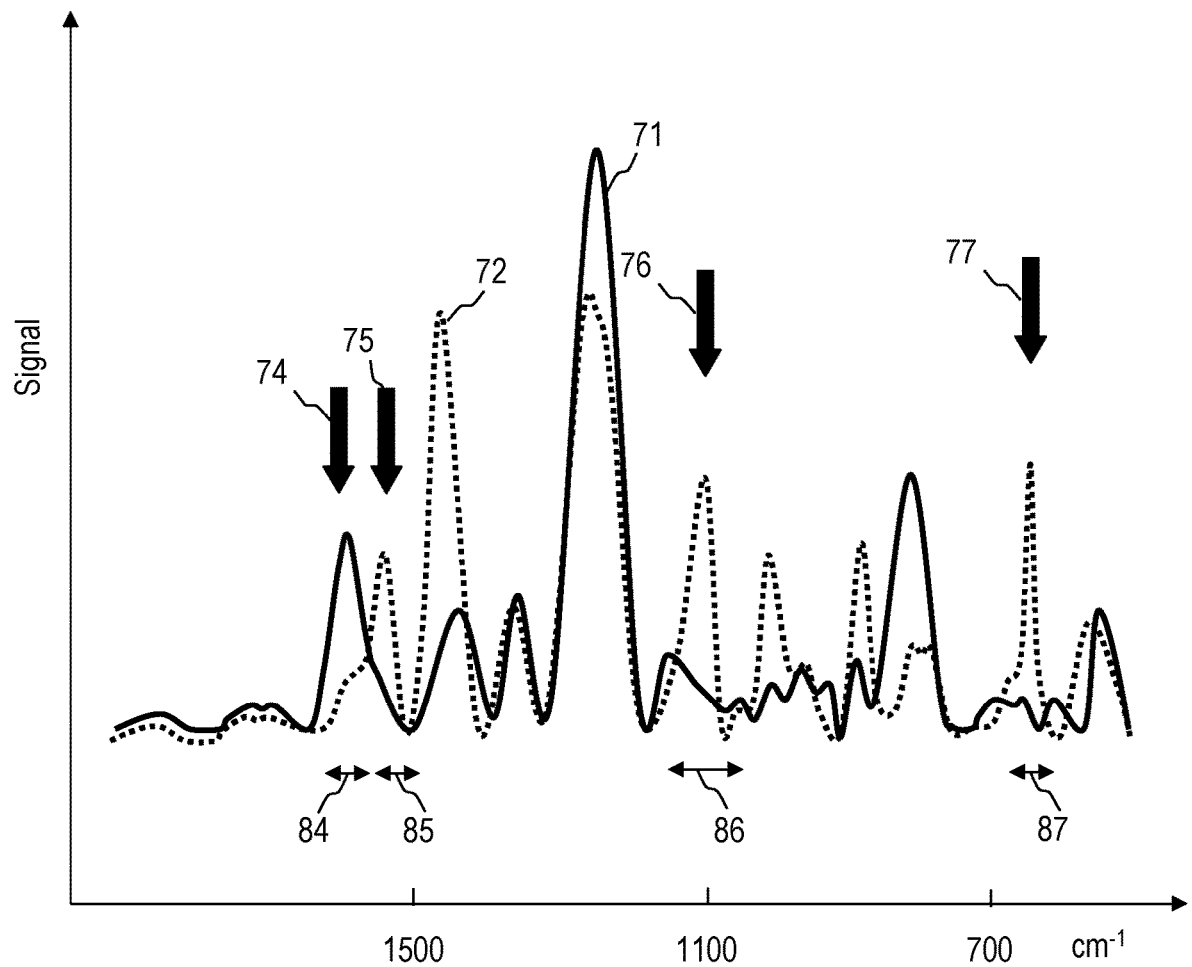
FIG. 9 shows a schematic illustration of Raman spectra which are evaluated by devices and methods according to exemplary embodiments.

FIG. 9 shows a Raman spectrum 71 of thrombocytes and a Raman spectrum 72 of erythrocytes. Mean value spectra are respectively illustrated according to storage of the blood-based product.

The position of Raman peaks enables a distinction of different cell types. For example, the Raman spectrum 71 of thrombocytes comprises Raman peaks in the case of a wavenumber or a plurality of wavenumbers 74, which enable a distinction of thrombocytes and other cell types. In a wavenumber range 84 or in a plurality of wavenumber ranges, which can reach for example from 1550 $cm^{-1}$ to 1590 $cm^{-1}$, a cell of the cell type thrombocytes can be identified from the presence of a Raman peak.

The Raman spectrum 72 of erythrocytes comprises Raman peaks in the case of wavenumbers 75, 76, 77, which allow a distinction between thrombocytes and other cell types. In a wavenumber range or in a plurality of wavenumber ranges 85, 76, 87, a cell of the cell type erythrocytes can be identified from the presence of a Raman peak. The one or plurality of wavenumber ranges 85, 86, 87 can be selected from the group consisting of a wavenumber range from 1480 $cm^{-1}$ to 1550 $cm^{-1}$, a wavenumber range from 1050 $cm^{-1}$ to 1120 $cm^{-1}$ and a wavenumber range from 600 $cm^{-1}$ to 700 $cm^{-1}$.

In order to distinguish different cell types and the functional modifications, to which the cells are respectively subjected, a cluster analysis can be performed, as has already been described above.

In addition to a determination of the proportions of cellular components of the blood-based products, which are subjected to functional modifications, impurities such as contaminations, bacteria or viruses can also be identified by the Raman spectroscopy.

With devices and methods according to exemplary embodiments, objective statements can be made regarding whether the blood reserve 2 may be used for a transfusion. The quantitative evaluation of the Raman spectrum provides objective information on the cells present and/or regarding whether the function of a significant proportion of erythrocytes or thrombocytes is impaired, for example by cell death or other processes. The quantitative evaluation of the Raman spectrum can, alternatively or additionally, be used in order to identify impurities and thus to verify the sterility of the blood reserve.

For the best possible evaluation even in the case of smaller sample quantities, the device 1 can be configured such that cells for example erythrocytes or thrombocytes are held in an optical trap in the case of the Raman spectroscopy. The optical trap can be produced by the excitation beam 17 of the Raman spectroscopy system 1 or a beam of electromagnetic radiation different therefrom.

Figure 10:
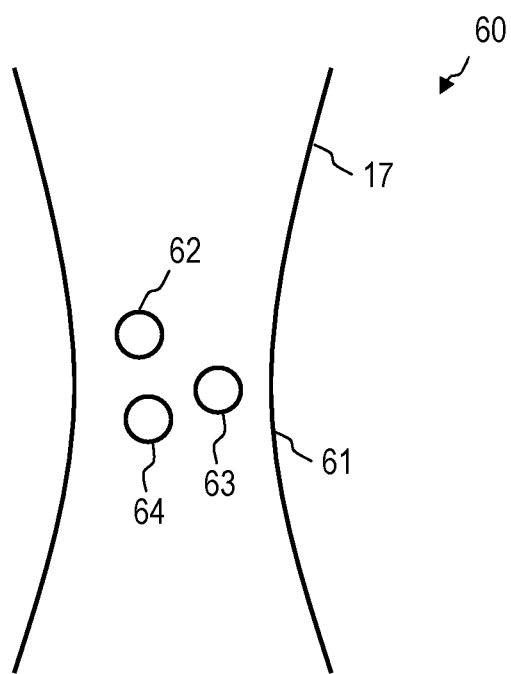
FIG. 10 shows a schematic illustration of the Raman spectroscopy in combination with an optical trap.

FIG. 10 shows, by way of example, a configuration 60 in the case of a device 1 according to an exemplary embodiment, in which biological objects are held in an optical trap in order to perform the Raman spectroscopy. A focal point 61 of a beam produces an optical trap potential, in which biological objects 62-64 are collected for the Raman spectroscopy. The focal point 61 can be produced by the excitation beam 17, which is output by the light source 11. The excitation beam 17 can thus be used both as excitation for the Raman scattering and for producing the optical trap. Alternatively, the optical trap can also be produced by a separate beam.

The Raman spectroscopy system 10 can also comprise a light conductor, for example an optical fibre, by means of which the excitation beam 17 and/or the Raman scattered light is guided. The light conductor can be positioned such that the excitation beam leaving said light conductor produces the optical trap with the focal point 61.

While exemplary embodiments have been described with reference to the figures, variations can be implemented in the case of further exemplary embodiments. For example, the Raman spectrum can be evaluated in a number of different wavenumber ranges or with a number of different methods of the spectral analysis in order to determine whether the blood-based product may be used for a transfusion. While exemplary embodiments have been described, in the case of which the sample is produced by removing it from a blood-based product, in the case of further exemplary embodiments the Raman spectroscopy can be performed on the blood reserve itself.

Figure 11:
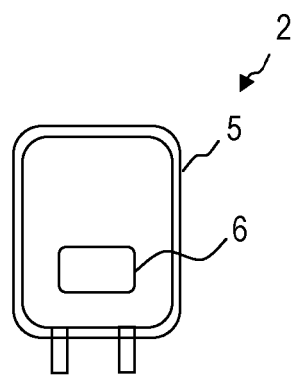
FIG. 11 shows a schematic illustration of a reserve which is configured for performing the method on the closed reserve.

FIG. 11 shows a blood reserve 2 with a bag 5 made from plastic material. For use in the case of methods or devices according to exemplary embodiments, the bag 5 can consist of a material which has high transmissivity for the excitation beam and the Raman scattered light of the relevant biological objects.

The bag 5 can comprise a window 6 made of a material which has high transmissivity for the excitation beam and the Raman scattered light of the relevant biological objects (for example erythrocytes, thrombocytes, bacteria and/or germs). The device 1 can comprise an object slide which is configured to receive the bag 5 such that the window 6 is positioned so as to allow the excitation beam from the light source 11 to pass through and the Raman scattered light to exit to the Raman spectrometer 14.

While devices and methods have been described in the context of quality controlling blood-based products with reference to FIG. 1 to FIG. 11, Raman spectroscopy can also be used in order to identify diseases or progressions of disease.

Accordingly, the device 1 from FIG. 1 can also be configured to process a blood sample 9 of a patient. The device 1 can evaluate the recorded Raman spectrum in order to identify a disease or a progression of disease. The device 1 can record and evaluate Raman spectra of a plurality of blood samples 9, which have been obtained in a time-sequential manner, in order to identify a progression of disease.

The device 1 can be configured to identify and evaluate, for example Raman peaks which are assigned to erythrocytes or thrombocytes. The device 1 can be configured to identify and evaluate, for example Raman peaks which are assigned to leukocytes.

By means of evaluating the recorded Raman spectrum or the recorded Raman spectra, an illness in the patient, from whom the blood sample 9 has been taken, can be identified. The evaluation can take place automatically by means of the device 1.

The device 1 can for example be configured to identify a disease or a progression of a disease which is selected from a group consisting of tumour diseases, blood coagulation disorders (e.g. PMH) or thrombosis. The device 1 can be configured to perform a spectral analysis of the recorded Raman spectrum or the recorded Raman spectra in order to identify the disease or the progression of disease.

Devices and methods according to exemplary embodiments can generally be used for quantitatively examining blood, for example for quality controlling blood reserves in blood banks.

The invention claimed is:

1. A method for quality controlling a blood-based product, wherein the method comprises:
    providing a computer comprising one or a plurality of processors or controllers;
    storing, in a database in a memory of the computer, a plurality of reference spectra, wherein the stored plurality of reference spectra includes one or more of:
        a position of Raman peaks and/or wavenumber ranges of fresh cells of different cell types of blood based products, wherein the blood-based products comprise one or more of an erythrocyte concentrate, a thrombocyte concentrate, a granulocyte concentrate, a leukocyte concentrate, whole blood and blood plasma;
        a position of Raman peaks and/or wavenumber ranges of functionally modified cells of the different cell types of the blood based products and
        information regarding ranges of multi-dimensional spaces of a cluster analysis, in which the reference spectra are respectively arranged;
    collecting, in an optical trap, at least one cell of a sample of a liquid blood-based product from one of the plurality of blood donors
    recording a Raman spectrum of the at least one cell of the sample by means of Raman spectroscopy;
    comparing the recorded Raman spectrum of the at least one cell of the sample with the plurality of reference spectra stored in the database;
    evaluating one or more of cell age, cell death, sterility, levels of impurity and cell functionality of the at least one cell of the sample based on results of the comparison; and
    determining whether the liquid blood-based product donated by the one of the plurality of blood donors is usable for a transfusion based on results of the evaluation.

2. The method according to claim 1,
wherein the evaluating includes identifying a functional modification of the at least one cell of the sample.

3. The method according to claim 2,
wherein the evaluating further comprises quantitatively determining which proportion of the at least one cell of the sample is subject to a functional modification.

4. The method according to claim 3,
wherein the quantitatively determining of which proportion of the at least one cell of the sample is subject to the functional modification further comprises respectively subjecting a plurality of recorded Raman spectra to a principal component analysis.

5. The method according to claim 1,
wherein the evaluating further comprises identifying the presence of bacteria or other impurities in the sample of the blood-based product.

6. The method according to claim 1,
wherein the evaluation comprises a spectral analysis of the Raman spectrum.

7. The method according to claim 1,
wherein the optical trap is produced by an excitation beam of a Raman spectroscopy system.

8. The method according to claim 1, comprising
wherein the at least one cell of the sample of the liquid blood-based product is selected from a group consisting of erythrocytes, thrombocytes, granulocytes and leukocytes.

9. The method according to claim 1, further comprising:
declaring the blood-based that has been tested by subjecting the sample to Raman spectroscopy usable; and transfusing a patient with the blood-based product.

10. The method according to claim 1, wherein:
    the collecting of the at least one cell of the sample of the liquid blood-based product includes collecting a plurality of cell types; and
    the evaluating includes identifying a functional modification of different categories of cells of the plurality of cell types.

11. The method according to claim 10, further comprising:
    recording several internal functional modifications of the different categories of cells.

* * * * *